United States Patent
Chen et al.

(10) Patent No.: US 9,469,580 B2
(45) Date of Patent: Oct. 18, 2016

(54) DEHYDROGENATION PROCESS

(71) Applicant: ExxonMobil Chemical Patents Inc., Baytown, TX (US)

(72) Inventors: Tan-Jen Chen, Kingwood, TX (US); Christopher L. Becker, Manhattan, KS (US); Hari Nair, Houston, TX (US); Francisco M. Benitez, Cypress, TX (US); Charles Morris Smith, Princeton, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/435,670

(22) PCT Filed: Nov. 18, 2013

(86) PCT No.: PCT/US2013/070468
§ 371 (c)(1),
(2) Date: Apr. 14, 2015

(87) PCT Pub. No.: WO2014/085112
PCT Pub. Date: Jun. 5, 2014

(65) Prior Publication Data
US 2015/0266795 A1  Sep. 24, 2015

Related U.S. Application Data

(60) Provisional application No. 61/732,118, filed on Nov. 30, 2012.

(30) Foreign Application Priority Data

Feb. 8, 2013 (EP) ..................................... 13154527

(51) Int. Cl.
| | | |
|---|---|---|
| C07C 45/00 | (2006.01) | |
| C07C 37/60 | (2006.01) | |
| C07C 2/74 | (2006.01) | |
| C07C 5/367 | (2006.01) | |
| C07C 45/29 | (2006.01) | |
| C07C 37/08 | (2006.01) | |
| C07C 45/53 | (2006.01) | |
| C07C 407/00 | (2006.01) | |
| B01J 23/62 | (2006.01) | |

(52) U.S. Cl.
CPC .............. *C07C 5/367* (2013.01); *B01J 23/626* (2013.01); *C07C 2/74* (2013.01); *C07C 37/08* (2013.01); *C07C 37/60* (2013.01); *C07C 45/294* (2013.01); *C07C 45/53* (2013.01); *C07C 407/00* (2013.01); *C07C 2101/14* (2013.01); *C07C 2521/08* (2013.01); *C07C 2523/14* (2013.01); *C07C 2523/42* (2013.01); *C07C 2523/62* (2013.01)

(58) Field of Classification Search
CPC ........ C07C 45/294; C07C 37/60; C07C 2/74
USPC .................. 568/342, 798; 585/252, 434, 467
See application file for complete search history.

(56) References Cited

U.S. PATENT DOCUMENTS

| | | |
|---|---|---|
| 2,908,656 A | 10/1959 | Hindin et al. |
| 4,094,918 A | 6/1978 | Murtha et al. |
| 4,122,125 A | 10/1978 | Murtha et al. |
| 4,177,165 A | 12/1979 | Murtha et al. |
| 4,206,082 A | 6/1980 | Murtha et al. |
| 5,053,571 A | 10/1991 | Makkee |
| 6,037,513 A | 3/2000 | Chang et al. |
| 7,579,511 B1 | 8/2009 | Dakka et al. |

FOREIGN PATENT DOCUMENTS

| | | |
|---|---|---|
| WO | 2009/131769 | 10/2009 |
| WO | 2011/096991 | 8/2011 |
| WO | 2011/096992 | 8/2011 |
| WO | 2011/096998 | 8/2011 |
| WO | 2012/082409 | 6/2012 |
| WO | 2012/134552 | 10/2012 |

*Primary Examiner* — Sikarl Witherspoon
(74) *Attorney, Agent, or Firm* — Siwen Chen; Stephen A. Baehl (57) ABSTRACT

Disclosed herein is a process for dehydrogenating a hydrocarbon with a dehydrogenation catalyst comprising a step of activating the catalyst precursor in a $H_2$-containing atmosphere. A particularly advantageous activation process includes heating the catalyst precursor to a temperature in a range from 400° C. to 600° C. The process of the present disclosure is particularly advantageous for dehydrogenating cyclohexane to make benzene.

20 Claims, 1 Drawing Sheet

DEHYDROGENATION PROCESS

PRIORITY CLAIM

This application is a National Stage Application of International Application No. PCT/US2013/070468 filed Nov. 18, 2013, which claims priority to U.S. Provisional Application Ser. No. 61/732,118 filed Nov. 30, 2012, and European Application No. 13154527.9 filed Feb. 8, 2013, the disclosures of which are fully incorporated herein by their reference.

CROSS REFERENCE TO RELATED APPLICATIONS

This patent application is related to U.S. Provisional Patent Application No. 61/468,298, filed on Mar. 28, 2011 and entitled "Dehydrogenation Process," and U.S. patent application Ser. No. 13/512,805, filed on Dec. 17, 2010 and entitled "Dehydrogenation Process," the contents of both of which are incorporated herein by reference in their entirety.

FIELD

The present invention relates to a process for dehydrogenating saturated cyclic hydrocarbons such as cyclohexane and/or methylcyclopentane, and in particular, cyclohexane and methylcyclopentane produced during hydroalkylation of benzene to cyclohexylbenzene.

BACKGROUND

Cyclohexylbenzene can be produced from benzene by the process of hydroalkylation or reductive alkylation. In this process, benzene is heated with hydrogen in the presence of a catalyst such that the benzene undergoes partial hydrogenation to produce a reaction intermediate such as cyclohexene which then alkylates the benzene starting material. Thus, U.S. Pat. Nos. 4,094,918 and 4,177,165 disclose hydroalkylation of aromatic hydrocarbons over catalysts which comprise nickel- and rare earth-treated zeolites and a palladium promoter. Similarly, U.S. Pat. Nos. 4,122,125 and 4,206,082 disclose the use of ruthenium and nickel compounds supported on rare earth-treated zeolites as aromatic hydroalkylation catalysts. The zeolites employed in these prior art processes are zeolites X and Y. In addition, U.S. Pat. No. 5,053,571 proposes the use of ruthenium and nickel supported on zeolite beta as the aromatic hydroalkylation catalyst. However, these earlier proposals for the hydroalkylation of benzene suffered from the problems that the selectivity to cyclohexylbenzene was low, particularly at economically viable benzene conversion rates, and that large quantities of unwanted by-products, particularly cyclohexane and methylcyclopentane, were produced.

More recently, U.S. Pat. No. 6,037,513 has disclosed that cyclohexylbenzene selectivity in the hydroalkylation of benzene can be improved by contacting the benzene and hydrogen with a bifunctional catalyst comprising at least one hydrogenation metal and a molecular sieve of the MCM-22 type. The hydrogenation metal is preferably selected from palladium, ruthenium, nickel, cobalt, and mixtures thereof, and the contacting step is conducted at a temperature of 50° C. to 350° C., a pressure of 100 kPa to 7000 kPa, a benzene to hydrogen molar ratio of 0.01 to 100 and a weight hourly space velocity (WHSV) of 0.01 $hr^{-1}$ to 100 $hr^{-1}$. The '513 patent discloses that the resultant cyclohexylbenzene can then be oxidized to the corresponding hydroperoxide and the peroxide decomposed to the desired phenol and cyclohexanone.

One disadvantage of this process is that it produces impurities such as cyclohexane and methylcyclopentane. These impurities represent loss of valuable benzene feed. Moreover, unless removed, these impurities will tend to build up in the system, thereby displacing benzene and increasing the production of undesirable by-products. Thus, a significant problem facing the commercial application of cyclohexylbenzene as a phenol precursor is removing the cyclohexane and methylcyclopentane impurities.

One solution to this problem is proposed in U.S. Pat. No. 7,579,511 which describes a process for making cyclohexylbenzene in which benzene undergoes hydroalkylation in the presence of a first catalyst to form a first effluent composition containing cyclohexylbenzene, cyclohexane, methylcyclopentane, and unreacted benzene. The first effluent composition is then separated into a cyclohexane/methylcyclopentane-rich composition, a benzene-rich composition, and a cyclohexylbenzene-rich composition and the cyclohexane/methylcyclopentane-rich composition is contacted with a second, low acidity, dehydrogenation catalyst to convert at least a portion of the cyclohexane to benzene and at least a portion of the methylcyclopentane to linear and/or branched paraffins and form a second effluent composition. The benzene-rich composition and the second effluent composition can then be recycled to the hydroalkylation step. However, one problem with this process is that cyclohexane and methylcyclopentane have similar boiling points to that of benzene so that their separation by conventional distillation is difficult.

Another solution is proposed in International Patent Publication No. WO2009/131769, in which benzene undergoes hydroalkylation in the presence of a first catalyst to produce a first effluent composition containing cyclohexylbenzene, cyclohexane, and unreacted benzene. The first effluent composition is then divided into a cyclohexylbenzene-rich composition and a $C_6$ product composition comprising cyclohexane and benzene. At least part of the $C_6$ product composition is then contacted with a second catalyst under dehydrogenation conditions to convert at least part of the cyclohexane to benzene and produce a second effluent composition which comprises benzene and hydrogen and which can be recycled to the hydroalkylation step.

Both of the processes disclosed in U.S. Pat. No. 7,579,511 and WO2009/131769 rely on the use of a dehydrogenation catalyst comprising a Group VIII metal on a porous inorganic support such as aluminum oxide, silicon oxide, titanium oxide, zirconium oxide, activated carbon, and combinations thereof. However, in practice, such a dehydrogenation catalyst has only limited activity for the conversion of cyclohexane and/or methylcyclopentane and in some instances can undergo rapid aging. There is therefore a need for an improved catalyst for removing cyclohexane and methylcyclopentane from the benzene recycle compositions employed in benzene hydroalkylation processes. Conversion of cyclohexane is especially important since its boiling point is within 1° C. of that of benzene. Conversion of methylcyclopentane is also desired but less important than cyclohexane since there is a difference of nearly 9° C. in the boiling point of methylcyclopentane and benzene.

More recently, it was discovered that catalyst containing at least one dehydrogenation metal (e.g., platinum or palladium) and a Group 1 or Group 2 metal promoter (i.e., alkali metal or alkaline earth metals) can be used to dehydrogenate cyclohexane and/or methylcyclopentane. This process is described, for example, in PCT Application No. PCT/US2010/061041, which was filed on Dec. 17, 2010. However, dehydrogenation catalysts having further improved cyclohexane conversion and/or selectivity are needed.

SUMMARY

It has now been found that an activation step of the dehydrogenation catalyst can markedly improve the performance of the catalyst.

A first aspect of the present disclosure relates to a dehydrogenation process, the process comprising:

(1A) providing a catalyst precursor comprising (i) an inorganic support, and (ii) 0.01 wt % to 10.0 wt % of a first metal selected from the Groups 6 to 10 metals of the Periodic Table of Elements based on the total weight of the catalyst precursor;

(1B) obtaining an activated dehydrogenation catalyst by treating the catalyst precursor at a temperature in a range from 300° C. to 600° C., preferably form 420° C. to 550° C., for a period of at least 15 minutes in a $H_2$-containing atmosphere; and (1C) contacting a first composition comprising cyclohexane with the activated dehydrogenation catalyst in a dehydrogenation reactor under a dehydrogenation condition to convert at least a portion of the cyclohexane to benzene and obtain a dehydrogenation reaction product.

A second aspect of the present disclosure relates to a process for making phenol and/or cyclohexanone, the process comprising:

(2A) producing cyclohexylbenzene using a process of the first aspect;

(2B) oxidizing at least a portion of the cyclohexylbenzene to obtain an oxidation reaction product comprising cyclohexylbenzene hydroperoxide; and (2C) cleaving at least a portion of the cyclohexylbenzene hydroperoxide to produce a cleavage reaction product comprising phenol and cyclohexanone.

The processes of the present disclosure have at least one or more of the following advantages. First, by heating a dehydrogenation catalyst precursor at an elevated temperature in a hydrogen-containing atmosphere before putting the catalyst precursor into dehydrogenation reaction, one can activate the catalyst precursor to obtain an activated catalyst with high conversion and selectivity. Second, by heating the catalyst precursor to an activation temperature higher than 400° C. during activation, one can surprisingly obtain a catalyst with improved conversion without sacrificing selectivity.

Additional features and advantages of the invention will be set forth in the detailed description and claims, as well as the appended drawings. It is to be understood that the foregoing general description and the following detailed description are merely exemplary of the invention, and are intended to provide an overview or framework to understanding the nature and character of the invention as it is claimed.

DETAILED DESCRIPTION

In the present disclosure, a process is described as comprising at least one "step." It should be understood that each step is an action or operation that may be carried out once or multiple times in the process, in a continuous or discontinuous fashion. Unless specified to the contrary or the context clearly indicates otherwise, each step in a process may be conducted sequentially in the order as they are listed, with or without overlapping with one or more other step, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are performed in the order as listed.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a hydrogenation metal" include embodiments where one, two, or more different types of the hydrogenation metals are used, unless specified to the contrary or the context clearly indicates that only one type of the hydrogenation metal is used.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question. All ranges expressed herein should include both end points as two specific embodiments unless specified or indicated to the contrary.

As used herein, the generic term "dicylcohexylbenzene" includes, in the aggregate, 1,2-dicyclohexylbenzene, 1,3-dicylohexylbenzene, and 1,4-dicyclohexylbenzene, unless clearly specified to mean only one or two thereof. The term cyclohexylbenzene, when used in the singular form, means mono substituted cyclohexylbenzene.

In the present disclosure, the composition of catalysts and precursors of catalysts are expressed on the basis of the dry components. To the extent that the catalyst materials may entrain water to different degrees, such water is not considered in its composition. While the catalyst materials or their precursors may be processed and/or used with a small quantity of water contained therein, it is preferred that the activated catalyst is dry (e.g., having a water content of at most 5.0 wt %, or at most 3.0 wt %, or at most 1.0 wt %, or at most 0.5 wt %, or at most 0.1 wt %) when put into use in a dehydrogenation process according to the present disclosure. In the present disclosure, the quantities of the first, second and third metals in the catalysts and precursors thereof are expressed on the basis of elemental metal, regardless of the oxidation state thereof. Thus, all quantities of Pt, Pd, Sn, K, Na, Ni, Co, and other Groups 1, 2, 6-10, and 14 metals in these catalyst materials are expressed an elemental basis, even though they may be present in the materials at issue in the form of, e.g., in whole or in part, salts, oxides, complexes, and elemental metals. For example, a catalyst composition made with 1.9 grams of tin chloride salt (1.0 gram of tin) and 22.29 grams of tetraamine platinum hydroxide solution (4.486 wt % Pt) that is supported on 98 grams of silicon dioxide contains 1.0 wt % of tin and 1.0 wt % Pt, based upon the total weight of the catalyst composition in dry components. Also, the composition of the precursor of a catalyst is expressed in terms of the final composition of the activated catalyst prepared therefrom. One having ordinary skill in the art of catalyst preparation can batch the starting materials, such as salts, solutions, oxides, and the like, to achieve a final target chemical composition of the activated catalyst. For example, in the present disclosure, a catalyst precursor comprising 1.0 wt % of Pt, 1.0 wt % Sn, and 98.0 wt % of silica means a precursor comprises the desired amount of starting materials such as one or more of $PtO_2$, Pt, $SnO_2$, SnO, $SnCl_4$, $SnCl_2$, and the like, that upon activation, would be converted into a final catalyst comprising platinum, tin, and silica in the above amounts.

The term "MCM-22 type material" (or "material of the MCM-22 type" or "molecular sieve of the MCM-22 type" or "MCM-22 type zeolite"), as used herein, includes one or more of:

molecular sieves made from a common first degree crystalline building block unit cell, which unit cell has the MWW framework topology. A unit cell is a spatial arrangement of atoms which if tiled in three-dimensional space describes the crystal structure. Such crystal structures are discussed in the "Atlas of Zeolite Framework Types," Fifth Edition, 2001, the entire content of which is incorporated as reference;

molecular sieves made from a common second degree building block, being a 2-dimensional tiling of such MWW framework topology unit cells, forming a monolayer of one unit cell thickness, desirably one c-unit cell thickness;

molecular sieves made from common second degree building blocks, being layers of one, or more than one, unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 type include those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques such as using the K-alpha doublet of copper as incident radiation and a diffractometer equipped with a scintillation counter and associated computer as the collection system.

Materials of the MCM-22 type include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), and MCM-56 (described in U.S. Pat. No. 5,362,697). Other molecular sieves, such as UZM-8 (described in U.S. Pat. No. 6,756,030), may be used alone or together with the MCM-22 type molecular sieves as well for the purpose of the present disclosure. Desirably, the molecular sieve is selected from (a) MCM-49; (b) MCM-56; and (c) isotypes of MCM-49 and MCM-56, such as ITQ-2.

The dehydrogenation catalyst employed in the dehydrogenation reaction comprises (i) an inorganic support; (ii) a first metal selected from Groups 6 to 10 of the Periodic Table of Elements; optionally (iii) a second metal selected from Group 14 of the Periodic Table of Elements; and optionally (iv) a third metal selected from Groups 1 and 2 of the Periodic Table of Elements. For example, the dehydrogenation catalyst may comprise both the first metal and the second metal, but is essentially free of the third metal. Examples of such catalyst are described in, e.g., WO2012/134552, the relevant portion of which is incorporated herein by reference. Alternatively, the dehydrogenation catalyst may comprise both the first and third metal, but is essentially free of the second metal. Examples of such catalyst are described in, e.g., WO2011/096998, the relevant portion of which is incorporated herein by reference. It is also possible, that the dehydrogenation catalyst used in the processes of the present disclosure comprises a first, a second, and a third metal simultaneously. As used herein, the numbering scheme for the Periodic Table Element Groups disclosed herein is the New Notation provided on the inside cover of Hawley's Condensed Chemical Dictionary (14$^{th}$ Edition), by Richard J. Lewis.

The catalyst used in the processes of the present disclosure comprises a first metal selected from Groups 6 to 10 of the Periodic Table of Elements, such as platinum and/or palladium. Typically, the metal selected from Groups 6 to 10 of the Periodic Table of Elements is present in an amount in a range from Fm1 wt % to Fm2 wt %, where Fm1 can be 0.01, 0.02, 0.03, 0.05, 0.08, 0.10, 0.30, 0.50, 0.80, 1.00, 1.50, 2.00, 2.50, 3.00, 3.50, 4.00, 4.50, or 5.00; and Fm2 can be 10.0, 9.50, 9.00, 8.50, 8.00, 7.50, 7.00, 6.50, 6.00, 5.50, 5.00, 4.50, 4.00, 3.50, 3.00, 2.50, 2.00, 1.50, or 1.00, to the extent Fm1<Fm2.

Alternatively or additionally, the catalyst used in the processes of the present disclosure may comprise (i) nickel at a concentration of at most 2.0 wt %, or at most 1.0 wt %, or at most 0.5 wt %, or at most 0.1 wt % nickel; and (ii) cobalt at a concentration of at most 2.0 wt %, or at most 1.0 wt %, or at most 0.5 wt %, or at most 0.1 wt %, the percentages based on the total weight of the catalyst. Preferably, the catalyst composition is free or substantially free of ruthenium, rhodium, lead, and/or germanium, and/or any other active elemental components.

Without intending to be bound by a particular theory, it is believed that the first metal in the activated catalyst is the primary component responsible for the dehydrogenation function of the catalyst. Under the proper dehydrogenation conditions, especially a desired temperature described in greater detail below, a cyclic hydrocarbon, especially a saturated compound such as cyclohexane, can be activated when in contact the first metal, undergo a dehydrogenation reaction, and be converted into a unsaturated compound such as benzene. It is also believed that at least part of the first metal of the activated catalyst used in the dehydrogenation processes of the present disclosure should be in elemental form in order to confer the desired level of dehydrogenation activities. Thus, it is desired that the activated catalyst, when in use in the dehydrogenation process, comprises at least x % of the first metal in element form, where x can be 50, 55, 60, 65, 70, 75, 80, 85, 90, 95, 98, 99, or even 99.5. It is also highly desired that, during a whole dehydrogenation reaction campaign according to the present disclosure, at least a majority of the first metal in the catalyst is maintained in elemental state. In an environment where hydrogen gas is abundant, such as in a typical dehydrogenation reactor in normal operation, such condition can be met. For example, the second metal, a Group 14 metal, is present in the activated dehydrogenation catalyst used in the dehydrogenation process of the present disclosure in an amount in a range of from Sm1 wt % to Sm2 wt %, based on the total weight of the dehydrogenation catalyst, where Sm1 can be 0.01, 0.02, 0.03, 0.05, 0.08, 0.10, 0.30, 0.50, 0.80, 1.00, 1.50, 2.00, 2.50, 3.00, 3.50, 4.00, 4.50, or 5.00; and Sm2 can be 10.0, 9.50, 9.00, 8.50, 8.00, 7.50, 7.00, 6.50, 6.00, 5.50, 5.00, 4.50, 4.00, 3.50, 3.00, 2.50, 2.00, 1.50, or 1.00, to the extent Sm1<Sm2. Preferably, the Group 14 metal is tin.

The ratio of the metal selected from Groups 6 to 10 of the Periodic Table of Elements to the metal selected from Group 14 of the Periodic Table of Elements (e.g., the Pt/Sn ratio) in the catalyst can be in a range from Rt1 to Rt2, where Rt1 can be 0.1, 0.2, 0.3, 0.4, 0.5, 0.8, 1.0, 2.0, 3.0, 4.0, 5.0, 8.0, 10.0, 15.0, 20.0, 30.0, 40.0, 50.0, and Rt2 can be 400, 350, 300, 250, 200, 150, 100, 90.0, 80.0, 70.0, 60.0, 50.0, to the extent Rt1<Rt2. Preferable ranges of the ratio are: from 2.5 to 400; from 2.7 to 200; and from 3.0 to 100.

Preferably, the activated catalyst used in the processes of the present disclosure comprises a third metal which is one or more of Group 1 and Group 2 of the Periodic Table of Elements. The third metal is present in an amount in a range from Tm1 wt % to Tm2 wt %, where Tm1 can be 0.1, 0.2, 0.3, 0.4, 0.5, 0.6, 0.7, 0.8, 0.9, 1.0, 1.5, 2.0, 2.5, 3.0; and Tm2 can be 5.0, 4.5, 4.0, 3.5, 3.0, 2.5, 2.0, 1.5, 1.0, as long as Tm1<Tm2. For example, the third metal may comprise a metal of the Group 1 elements of the Periodic Table of Elements, such as potassium, cesium, and rubidium; preferably potassium. Still alternatively, the third metal may include at least one Group 2 element of the Periodic Table of Elements such as beryllium, calcium, magnesium, strontium, barium, and radium; preferably calcium and magnesium. Given the high chemical activities of the Groups 1 and 2 elements in the Periodic Table of Elements, the third metal in the catalyst used in the processes of the present disclosure are mostly likely present in an oxidation state higher than 0, such as +1, +2, and the like, in the form of oxides, salts, sulfides, hydrides, and the like.

It will be understood that the first metal, second metal, and third metal may not be purely the elemental metal, but could, for example, be at least partly in another form, such as a salt, oxide, chloride, hydride, sulfide, carbonate, etc., even though the composition of the catalyst is expressed in terms of elemental metals for the first, second, and third metals.

The activated dehydrogenation catalyst used in the dehydrogenation processes of the present disclosure further comprises an inorganic support. For example, the dehydrogenation catalyst support may comprise one or more of silica, alumina, a silicate, an aluminosilicate, zirconia, carbon, or carbon nanotubes. Alternatively, the support may comprise an inorganic oxide such as one or more of silicon dioxide, titanium dioxide, and zirconium dioxide. The support may or may not comprise a binder. Impurities that can be present in the catalyst support are, for example, sodium salts such as sodium silicate, which can be present from anywhere from 0.01 wt % to 2 wt %. Suitable silica supports are described in, for example, PCT Pub. No. WO/2007084440 A1 filed on Jan. 12, 2007, and entitled "Silica Carriers" and is hereby incorporated by reference for this purpose.

The dehydrogenation catalyst may comprise a silica support having pore volumes and median pore diameters determined by the method of mercury intrusion porosimetry described by ASTM Standard Test D4284. The silica support may have surface areas as measured by ASTM D3663. The pore volumes may be in the range from about 0.2 cc/gram to about 3.0 cc/gram. The median pore diameters are in the range from about 10 angstroms to about 2000 angstroms, or from 20 angstroms to 500 angstroms; and the surface areas ($m^2$/gram) are in the range from 10 to 1000 $m^2$/gram, or from 20 to 500 $m^2$/gram. The support may or may not comprise a binder.

For example, the dehydrogenation catalyst precursor can be prepared by sequentially or simultaneously treating the support, such as by impregnation, with one or more liquid compositions comprising the first metal or a precursor thereof, the second metal or a precursor thereof, and/or the third metal or precursor thereof, and an optional inorganic base component or a precursor in a liquid carrier, such as water. An organic dispersant may be added to each liquid carrier to assist in uniform application of the metal component(s) to the support. Suitable organic dispersants include amino alcohols and amino acids, such as arginine. For example, the organic dispersant may be present in the liquid composition in an amount between 1.0 wt % and 20 wt % of the liquid composition.

The catalyst may comprise a first metal and a second metal, but is essentially free of the third metal, and the catalyst precursor can be prepared by sequential impregnation with the second metal precursor being applied to the support before the Group 6-10 metal component.

After treatment with the liquid composition, the inorganic support can be heated in one or more stages, generally at a temperature of 100° C. to 700° C. for a time of 0.5 to 50 hours, to effect one or more of: (a) removal of the liquid carrier; (b) conversion of a metal component to a catalytically active form; and (c) decompose the organic dispersant. The heating may be conducted in an oxidizing atmosphere, such as air. A catalyst precursor is thus obtained.

The catalyst precursor may comprise the first metal in one or more oxidation states, such as in elemental form, a salt, an oxide, and the like. Where the catalyst precursor is prepared by a step of calcination in the air or other $O_2$-containing atmosphere, at least a part of the first metal, the optional second and third metals are in an oxidized form. For example, if the catalyst comprises Pt and Sn and a silica support, and the precursor is prepared by impregnating the silica support by a Pt salt and Sn salt solution followed by drying and calcination in air, the catalyst precursor would typically comprise at least a part of Pt in the form of $PtO_2$, and a part of Sn in the form of $SnO_2$.

In the processes of the present disclosure, the catalyst precursor is subject to a step of activation prior to being used in a dehydrogenation reaction. The activation involves heating the catalyst precursor in a reducing atmosphere comprising $H_2$ at an elevated temperature. The reducing atmosphere can be pure hydrogen, or a mixture of hydrogen with other reducing or inert gas, such as $N_2$, $CH_4$, $C_2H_5$, other hydrocarbons, and the like. Preferably, the $H_z$-containing atmosphere used for the activation step prior to contacting the catalyst precursor is a substantially dry stream of gas comprising $H_2O$ at no more than aa vol %, where aa can be 5.0, 4.0, 3.0, 2.0, 1.0, 0.8, 0.5, 0.3, 0.1, 0.05, 0.01, 0.005, 0.001, 0.0005, or even 0.0001. The dry $H_2$ stream can serve to heat the catalyst precursor, dry the precursor before significant reduction occurs, and purging the H₂O produced during reduction, if any. Upon contacting with hydrogen at high temperature, the first metal, if in an oxidation state higher than elemental, would be at least partly reduced to a lower oxidation state, advantageously elemental state. For example, PtO₂ and PdO can be reduced to Pt and Pd by H₂ at an elevated temperature. The second metal, if in an oxidation state higher than elemental, may be reduced to a lower oxidation state or elemental state as well in the activation step by hydrogen and/or other components in the activation atmosphere. The third metal, however, being a Group 1 or 2 metal in the Periodic Table such as K, Na, Ca, and the like, if present in the catalyst, would most likely remain in an oxidation state higher than elemental in the activated catalyst in the form of oxide, salt, or part of complex material such as a glass or ceramic material formed with the inorganic support material.

During the activation step, the catalyst precursor may be heated from a lower temperature, e.g., room temperature, to a target activation temperature. As used herein, "activation temperature" means the highest temperature the catalyst precursor is exposed to for at least 3 minutes (or at least 5 minutes, or at least 10 minutes, or at least 15 minutes, or at least 20 minutes) during activation. It is highly desired that the catalyst precursor is surrounded by a H₂-containing atmosphere during the heating step. The temperature heating rate of the catalyst precursor can be in a range from HR1° C./minute to HR2° C./minute, where HR1 can be 2, 4, 5, 6, 8, 10, 12, 14, 15, and HR2 can be 50, 45, 40, 35, 34, 32, 30, 28, 26, 25, 24, 22, 20, or 18. When the temperature is relatively low, e.g., lower than 100° C., reducing of the first and/or second and/or third metal(s) can be slow and negligible. The higher the temperature of the catalyst precursor, the higher the rate of the reducing reactions. Thus, it is desired that the highest temperature the catalyst precursor is exposed to (and thus, reached) during the activation step is not lower than T1° C., where T1 can be 300, 320, 340, 350, 360, 380, 400, 420, 440, 450. It is highly desired that the catalyst precursor is held within the temperature range from Tact—20° C. to Tact for an activation duration of at least D1 minutes, where Tact is the activation temperature, and D1 can be 10, 15, 20, 25, 30, 45, 60, 75, 90, 120, 150, 180, 240, 300, 360, 420, 480, 540, 600, 660, 720, 780, 840, or even 900. However, it was found that too high an activation temperature and too long a temperature hold period around the maximal temperature can be detrimental to the performance of the activated catalyst. Without intending to be bound by a particular theory, it is believed that the first and second metals in elemental form may be mobilized on the surface of the inorganic support at very high temperature, agglomerate to form large crystals, thereby reducing the number of effective sites on the activated catalyst. Thus, it is desired that the activation temperature the catalyst precursor is exposed to in the activation step is not higher than T2° C., where T2 can be 650, 640, 630, 620, 610, 600, 590, 580, 570, 560, 550, 540, 530, 520, 510, and even 500. It is desired that during the heating step and the temperature hold period, the catalyst precursor is exposed to a H₂-containing atmosphere at least b % of the time, where b can be 50, 60, 70, 80, 90, 95, 98, or even 100%. When and if the catalyst precursor is not surrounded by an H₂-containing atmosphere, it is highly desired that it is surrounded by an otherwise reducing or inert atmosphere, such as CH₄, N₂, and mixtures thereof, and the like.

It has been found that, in a surprising manner, an activation temperature in the range of 300° C. to 600° C. is particularly advantageous, especially for those catalysts comprising Pt and/or Pd as the first metal, and a second metal such as Sn. Data showed that cyclohexane dehydrogenation using those catalysts activated at such high temperature demonstrated notably higher conversion of cyclohexane to benzene, all without sacrificing the selectivity. Thus, preferably, the catalyst precursor containing Pt and Sn is activated at an activation temperature in a range from Ta1° C. to Ta2° C., where Ta1 and Ta2 can be, independently, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, or 600, as long as Ta1<Ta2.

At the end of the temperature holding period around the activation temperature, it is desired that at least y % of all of the first and second metals in the catalyst precursor have been reduced to the desired oxidation state, such as elemental state, where y can be 50, 55, 60, 65, 70, 75, 80, 85, 90, 95, 98, 99, 99.5, 99.8, or even 99.9. Where the catalyst comprises Pt and/or Pd, it is desired that at least y % of Pt and/or Pd are reduced to elemental Pt and Pd at the end of the temperature holding period. Where the catalyst comprises Sn, it is desired that at least z % of Sn is reduced to elemental Sn at the end of the temperature holding period, where z can be 40, 45, 50, 55, 60, 65, 70, 75, 80, 85, 90, 95, 98, or even 99.

At the end of the temperature holding step, the catalyst precursor is mostly, and preferably substantially all, converted into an activated catalyst. The activated catalyst at this stage may be at a temperature higher or lower than or substantially the same as the use temperature of the activated catalyst in the dehydrogenation process. The catalyst may then be put into the dehydrogenation reactions after further heating or cooling accordingly where needed. In any event, it is highly desired that the activated catalyst is protected from oxidation before use. To that end, during a gap, if any, between the completion of activation and the start of the dehydrogenation reaction, it is desired that the activated catalyst is protected by a H₂-containing or inert atmosphere the same or different from the atmosphere used in the activation step. It is particularly advantageous to conduct the activation step and the dehydrogenation step in the same reactor, eliminating the need of transporting the activated catalyst to the dehydrogenation reactor and complications caused.

The activated dehydrogenation catalyst may have an oxygen chemisorption value (ocv) of greater than ocv1%, where ocva can be 5, 8, 12, 15, 18, 20, 22, 25, 28, or 30. As used herein, the oxygen chemisorption value (ocv) of a particular catalyst is a measure of metal dispersion on the catalyst and is defined as:

$$OCV = \frac{\text{amount of oxygen sorbed by the catalyst in moles}}{\text{amount of dehydrogenation metal contained in the catalyst in moles}} \times 100\%.$$

The oxygen chemisorption values referred to herein are measured using the Micromeritics ASAP 2010 physisorption analyzer as follows. Approximately 0.3 to 0.5 grams of catalyst are placed in the Micrometrics device. Under flowing helium, the catalyst is ramped from ambient (18° C.) to 250° C. at a rate of 10° C. per minute and held for 5 minutes. After 5 minutes, the sample is placed under vacuum at 250° C. for 30 minutes. After 30 minutes of vacuum, the sample is cooled to 35° C. at 20° C. per minute and held for 5 minutes. The oxygen and hydrogen isotherm is collected in increments at 35° C. between 0.50 and 760 mm Hg. Extrapolation of the linear portion of this curve to zero pressure gives the total (i.e., combined) adsorption uptake.

Preferably, the alpha value of the dehydrogenation catalyst is from 0 to 10, and from 0 to 5, and from 0 to 1. The alpha value of the support is an approximate indication of the catalytic cracking activity of the catalyst compared to a standard catalyst. The alpha test gives the relative rate constant (rate of normal hexane conversion per volume of catalyst per unit time) of the test catalyst relative to the standard catalyst which is taken as an alpha of 1 (Rate Constant=0.016 s$^{-1}$). The alpha test is described in U.S. Pat. No. 3,354,078 and in J. Catalysis, 4, 527 (1965); 6, 278 (1966); and 61, 395 (1980), to which reference is made for a description of the test. The experimental conditions of the test used to determine the alpha values referred to in this specification include a constant temperature of 538° C., and a variable flow rate as described in detail in J. Catalysis, 61, 395 (1980). Alternatively, the alpha value may range from valpha1 to valph2, where valpha1 can be 0.0, 0.1, 0.2, 0.3, 0.4, 0.5, 0.6, 0.7, 0.8, 0.9, 1, 2, 3, 4, 5, 6, 7, 8, 9, and 10; and valpha2 can be 200, 175, 150, 125, 100, 90, 80, 70, 60, 50, 40, 30, 20, 10, 5, 1.9, 1.8, 1.7, 1.6, 1.5, 1.4, 1.3, 1.2, 1.1, 1, 0.9, 0.8, 0.7, 0.6, and 0.5, as long as valpha1<valpha2.

The activated dehydrogenation catalyst made by using the method of the present disclosure can be used for dehydrogenating a first composition comprising any dehydrogenable hydrocarbon materials such as those containing a cyclic hydrocarbon compound. Preferably, the first composition comprises a cyclic hydrocarbon compound, such as cyclopropane, cyclobutane, cyclopentane, cyclohexane, cycloheptane, cyclooctane, cyclododecane, cyclodecane, cycloundecane, and derivatives (such as alkylated derivatives) thereof. The first composition may comprise C1 wt % to C2 wt % of a saturated cyclic hydrocarbon (e.g., cyclohexane), where C1 and C2 can be, independently, 0.1, 0.2, 0.3, 0.4, 0.5, 0.6, 0.7, 0.8, 0.9, 1.0, 3.0, 5.0, 8.0, 10.0, 15.0, 20.0, 25.0, 30.0, 35.0, 40.0, 45.0, 50.0, 55.0, 60.0, 70.0, 75.0, 80.0, 85.0, 90.0, 95.0, 98.0, as long as C1<C2, where the percentages are based on the total weight of the first composition contacting the activated catalyst.

Where the first composition comprises a six-membered cyclic hydrocarbon such as cyclohexane, it may further comprise one or more five-membered ring cyclic hydrocarbon (such as cyclopentane, methylcyclopentane, ethylcyclopentane, and the like), at a concentration based on the total weight of the first composition in a range from C3 wt % to C4 wt %, where C3 and C4 can be, independently, 0.01, 0.03, 0.05, 0.08, 0.10, 0.15, 0.20, 0.25, 0.30, 0.35, 0.40, 0.45, 0.50, 0.60, 0.70, 0.80, 0.90, 1.00, 1.50, 2.00, 2.50, 3.00, 3.50, 4.00, 4.50, 5.00, as long as C3<C4.

The first composition may further comprise a non-dehydrogenable component, such as an aromatic hydrocarbon, at a concentration based on the total weight of the first composition in a range from C5 wt % to C6 wt %, where C5 and C6 can be, independently, 5, 8, 10, 15, 20, 25, 30, 35, 40, 45, 50, 55, 60, 65, 70, 75, 80, 85, 90, or 95, as long as C1<C2. The aromatic hydrocarbon may be, for example, benzene. The aromatic hydrocarbon can be the same as the product of the dehydrogenation process using the activated dehydrogenation catalyst of the present disclosure. The non-dehydrogenable component in the first composition can serve as the heat carrier need for maintaining the dehydrogenation reaction at a desired temperature and reaction rate.

Suitable conditions for the dehydrogenation step include a temperature of 100° C. to 1000° C., a pressure of atmospheric to 100 kPa-gauge to 7000 kPa-gauge (kPag), and a weight hourly space velocity of 0.2 hr$^{-1}$ to 50 hr$^{-1}$.

Preferably, the temperature of the dehydrogenation process can be from Td1° C. to Td2° C., where Td1 can be 100, 150, 200, 250, 300, 350, 400, 450, 500, 550, 600; and Td2 can be 1000, 950, 900, 850, 800, 750, 700, 650, 600, or 550, as long as Td1<Td2.

Preferably, the pressure of the dehydrogenation process can be from P1 kPa (gauge) to P2 kPa (gauge), where P1 and P2 can be, independently, 0, 100, 150, 200, 250, 300, 350, 400, 450, 500, 600, 700, 800, 900, 1000, 1500, 2000, 2500, 3000, 4000, 5000, 6000, or 7000.

The reactor configuration used for the dehydrogenation process may comprise one or more fixed bed reactors containing a solid catalyst with a dehydrogenation function. Per-pass conversion of the saturated cyclic hydrocarbon (e.g., cyclohexane) using the present catalyst can be at least con %, where con can be 70, 75, 80, 85, 90, 95, or even 98. The reaction is endothermic. Typically temperature of the reaction mixture drops across a catalyst bed because of the endothermic effect. External heat may be supplied through one or more heat exchangers to the reactant in the reactor to maintain the temperature of the reactant in the desired range. The temperature of the reaction composition drops across each catalyst bed, and then is raised by the heat exchangers. Preferably, 1 to 5 beds are used, with a temperature drop of 30° C. to 100° C. across each bed. Preferably, the last bed in the series runs at a higher exit temperature than the first bed in the series.

Although the present process can be used with any composition comprising a saturated cyclic hydrocarbon (e.g., cyclohexane) and, optionally a five-membered ring compound (e.g., methylcyclopentane), the process has particular application as part of an integrated process for the conversion of benzene to phenol. In such an integrated process the benzene is initially converted to cyclohexylbenzene by any conventional technique, including alkylation of benzene with cyclohexene in the presence of an acid catalyst, such as zeolite beta or an MCM-22 type molecular sieve, or by oxidative coupling of benzene to biphenyl followed by hydrogenation of the biphenyl. However, in practice, the cyclohexylbenzene is generally produced by contacting the benzene with hydrogen under hydroalkylation conditions in the presence of a hydroalkylation catalyst whereby the benzene undergoes the following reaction (1) to produce cyclohexylbenzene (CHB):

(1)

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are from 100° C. to 400° C., such as from 125° C. to 250° C., while suitable reaction pressures (gauge) are from 100 kPa to 7,000 kPa, such as from 500 kPa to 5,000 kPa. Suitable values for the molar ratio of hydrogen to benzene are between 0.15:1 and 15:1, such as between 0.4:1 and 4:1 for example, between 0.4:1 and 0.9:1.

The catalyst employed in the hydroalkylation reaction is generally a bifunctional catalyst comprising a molecular sieve of the MCM-22 type described above and a hydrogenation metal.

Any known hydrogenation metal can be employed in the hydroalkylation catalyst, although suitable metals include palladium, ruthenium, nickel, zinc, tin, and cobalt, with palladium being particularly advantageous. The amount of hydrogenation metal present in the catalyst can be in a range from 0.05 wt % to 10 wt %, such as from 0.1 wt % to 5.0 wt %, of the catalyst. Where the MCM-22 type molecular sieve is an aluminosilicate, the amount of hydrogenation metal present is such that the molar ratio of the aluminum in the molecular sieve to the hydrogenation metal is preferably from 1.5 to 1500, for example, from 75 to 750, such as from 100 to 300.

The hydrogenation metal may be directly supported on the MCM-22 type molecular sieve by, for example, impregnation or ion exchange. Preferably, at least 50 wt %, for example at least 75 wt %, and generally substantially all of the hydrogenation metal is supported on an inorganic oxide separate from, but composited with the molecular sieve. In particular, it is found that by supporting the hydrogenation metal on the inorganic oxide, the activity of the catalyst and its selectivity to desired products such as cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia.

The hydrogenation metal can be deposited on the inorganic oxide, such as by impregnation, before the metal-containing inorganic oxide is composited with the molecular sieve. Typically, the catalyst composite can be produced by co-pelletization, in which a mixture of the molecular sieve and the metal-containing inorganic oxide are formed into pellets at high pressure (generally 350 kPa to 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite. Alternatively, the molecular sieve, the inorganic oxide, and the optional binder can be composited and formed into pellets by, e.g., extrusion, which is then impregnated by the one or more dispersions, such as solutions, containing one or more of the metals.

The catalyst may comprise a binder. Suitable binder materials include synthetic or naturally occurring substances as well as inorganic materials such as clay, silica, and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins, commonly known as Dixie, McNamee, Ga., and Florida clays or others in which the main mineral constituent is halloysite, kaolinite, dickite, nacrite, or anauxite. Such clays can be used in the raw state as originally mined or initially subjected to calcination, acid treatment, or chemical modification. Suitable metal oxide binders include silica, alumina, zirconia, titania, silica-alumina, silica-magnesia, silica-zirconia, silica-thoria, silica-beryllia, silica-titania, as well as ternary compositions such as silica-alumina-thoria, silica-alumina-zirconia, silica-alumina-magnesia, and silica-magnesia-zirconia.

Although the hydroalkylation step is highly selective towards cyclohexylbenzene, the effluent from the hydroalkylation reaction will normally contain unreacted benzene feed, some dialkylated products, and other by-products, particularly cyclohexane, and methylcyclopentane. In fact, typical selectivities to cyclohexane and methylcyclopentane in the hydroalkylation reaction are 1-25 wt % and 0.1-2.0 wt %, respectively.

The dehydrogenation reaction can be performed on all or a portion of the output of the hydroalkylation step.

Alternatively, the hydroalkylation reaction effluent is separated into at least a (i) C6-rich composition; and (ii) the remainder of the hydroalkylation reaction effluent. When a composition is described as being "rich in" in a specified species (e.g., C6-rich, benzene-rich or hydrogen-rich), it is meant that the wt % of the specified species in that composition is enriched relative to the feed composition (i.e., the input). A "$C_6$" species generally means any species containing 6 carbon atoms.

Given the similar boiling points of benzene, cyclohexane, and methylcyclopentane, it is difficult to separate these materials by distillation. Thus, a $C_6$-rich composition comprising benzene, cyclohexane, and methylcyclopentane may be separated by distillation from the hydroalkylation reaction effluent. This $C_6$-rich composition can be then subjected to the dehydrogenation process described above such that at least a portion of the cyclohexane in the composition is converted to benzene and at least a portion of the methylcyclopentane is converted to linear and/or branched paraffins, such as 2-methylpentane, 3-methylpentane, n-hexane, and other hydrocarbon components such as isohexane, $C_5$ aliphatics, and $C_1$ to $C_4$ aliphatics. The dehydrogenation product composition may then be fed to a further separation system, typically a further distillation tower, to divide the dehydrogenation product composition into a benzene-rich stream and a benzene-depleted stream. The benzene-rich stream can then be recycled to the hydroalkylation step, while the benzene-depleted stream can be used as a fuel for the process. When a composition is described as being "depleted" with respect to a particular species (e.g., benzene-depleted), it is meant that the wt % of the specified species in that composition is depleted relative to the feed composition (i.e., the material charged into the reactor).

After separation of the $C_6$-rich composition, the remainder of hydroalkylation reaction effluent may be fed to a second distillation tower to separate the monocyclohexylbenzene product (e.g., cyclohexylbenzene) from any dicyclohexylbenzene and other heavies. Depending on the amount of dicyclohexylbenzene present in the reaction effluent, it may be desirable to transalkylate the dicyclohexylbenzene with additional benzene to maximize the production of the desired monoalkylated species.

Transalkylation with additional benzene may be effected in a transalkylation reactor, separate from the hydroalkylation reactor, over a suitable transalkylation catalyst, including large pore molecular sieves such as a molecular sieve of the MCM-22 type, zeolite beta, MCM-68 (see U.S. Pat. No. 6,014,018), zeolite Y, zeolite USY, and mordenite. A large pore molecular sieve may have an average pore size of at least 7 Å, such as from 7 Å to 12 Å. The transalkylation reaction is typically conducted under at least partial liquid phase conditions, which suitably include a temperature of 100° C. to 300° C., a pressure of 800 kPa to 3500 kPa, a weight hourly space velocity of 1 $hr^{-1}$ to 10 $hr^{-1}$ on total feed, and a benzene/dicyclohexylbenzene weight ratio of 1:1 to 5:1. The transalkylation reaction effluent can then be returned to the second distillation tower to recover the additional monocyclohexylbenzene product produced in the transalkylation reaction.

After separation in the second distillation tower, the cyclohexylbenzene can be converted into phenol and cyclohexanone by a process similar to the Hock process. In this process, cyclohexylbenzene is initially oxidized to the corresponding hydroperoxide. This is accomplished by introducing an oxygen-containing gas, such as air, into a liquid phase containing the cyclohexylbenzene. Unlike the Hock process, atmospheric air oxidation of cyclohexylbenzene, in the absence of a catalyst, is very slow and hence the oxidation is normally conducted in the presence of a catalyst.

Suitable catalysts for the cyclohexylbenzene oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt, or N-hydroxy-o-benzenedisulphonimide. Preferably, the catalyst is N-hydroxyphthalimide. Another suitable catalyst is N,N',N"-trihydroxyisocyanuric acid.

These materials can be used either alone or in the presence of a free radical initiator and can be used as liquid-phase, homogeneous catalysts or can be supported on a solid carrier to provide a heterogeneous catalyst. Typically, the N-hydroxy substituted cyclic imide or the N,N',N"-trihydroxyisocyanuric acid is employed in an amount between 0.0001 wt % to 15 wt %, such as between 0.001 wt % to 5.0 wt %, of the cyclohexylbenzene.

Suitable conditions for the oxidation step include a temperature between 70° C. and 200° C., such as 90° C. to 130° C., and a pressure of 50 kPa to 10,000 kPa. Any oxygen-containing gas, preferably air, can be used as the oxidizing agent. The reaction can take place in batch reactors or continuous flow reactors. A basic buffering agent may be added to react with acidic by-products that may form during the oxidation. In addition, an aqueous phase may be introduced, which can help dissolve basic compounds, such as sodium carbonate.

Another reactive step in the conversion of the cyclohexylbenzene into phenol and cyclohexanone involves cleavage of the cyclohexylbenzene hydroperoxide, which is conveniently effected by contacting the hydroperoxide with a catalyst in the liquid phase at a temperature of 20° C. to 150° C., such as 40° C. to 120° C., and a gauge pressure of 50 kPa to 2,500 kPa, such as 100 kPa to 1000 kPa. The cyclohexylbenzene hydroperoxide is preferably diluted in an organic solvent inert to the cleavage reaction, such as methyl ethyl ketone, cyclohexanone, phenol or cyclohexylbenzene, to assist in heat removal. The cleavage reaction can be conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid, and p-toluenesulfonic acid. Ferric chloride, boron trifluoride, sulfur dioxide, and sulfur trioxide are also effective homogeneous cleavage catalysts. The preferred homogeneous cleavage catalyst is sulfuric acid, with preferred concentrations in the range of 0.05 wt % to 0.5 wt %. For a homogeneous acid catalyst, a neutralization step preferably follows the cleavage step. Such a neutralization step typically involves contact with a basic component, with subsequent removal of a salt-enriched phase by decanting or distillation.

A suitable heterogeneous catalyst for use in the cleavage of cyclohexylbenzene hydroperoxide includes a clay, such as an acidic montmorillonite silica-alumina clay, as described in U.S. Pat. No. 4,870,217, or a faujasite molecular sieve as described in WO2012/145031.

The effluent from the cleavage reaction comprises phenol and cyclohexanone in substantially equimolar amounts and, depending on demand, the cyclohexanone can be sold or can be dehydrogenated into additional phenol. Any suitable dehydrogenation catalyst can be used in this reaction, such as the dehydrogenation catalyst or a variation of the catalyst described herein. Suitable conditions for the dehydrogenation step comprise a temperature of 250° C. to 500° C. and a pressure of 0.01 atm to 20 atm (1 kPa to 2030 kPa), such as a temperature of 300° C. to 450° C. and a pressure of 1 atm to 3 atm (100 kPa to 300 kPa).

The invention will now be more particularly described with reference to the following non-limiting examples and the accompanying drawings.

EXAMPLES

In the examples, a catalyst precursor comprising Pt as the first metal, Sn as the second metal, $SiO_2$ as the inorganic support and essentially free of a third metal, was activated at various temperatures in the presence of a flowing $H_2$ stream, and then tested for activities in the dehydrogenation of cyclohexane under nominally identical dehydrogenation conditions in a tubular down-flow reactor. Method of making the catalyst precursor was disclosed in WO2012/134552, the content of which is incorporated herein by reference in its entirety.

Procedure A:

The catalyst was activated by ramping from room temperature to 400° C. at a rate of 40° C./hour and holding the catalyst at the final temperature for 2 hours. The activation was conducted at 100 psig (689 kPa gauge) with pure hydrogen.

Procedure B:

The catalyst was activated by ramping from room temperature to 400° C. at a rate of 15° C./hour. The catalyst was further activated by ramping from 400° C. to 520° C. at a rate of 5° C./hour and holding the catalyst at the final temperature for 8 hours. The activation was also conducted at 100 psig (689 kPa gauge) with pure hydrogen.

Upon activation, the catalysts were then tested with a feed comprising 10 wt % cyclohexane, 1 wt % methylcyclopentane, and 89 wt % benzene at 420° C., 109 psig (752 kPa gauge) and $H_2$/Hydrocarbon molar ratio at 4. Key results from the activation study are summarized in FIG. 1 and FIG. 2, where 101 represents the results for the catalyst prepared according to Procedure A, and 103 represents the results for the catalyst prepared according to Procedure B.

Figure 1:
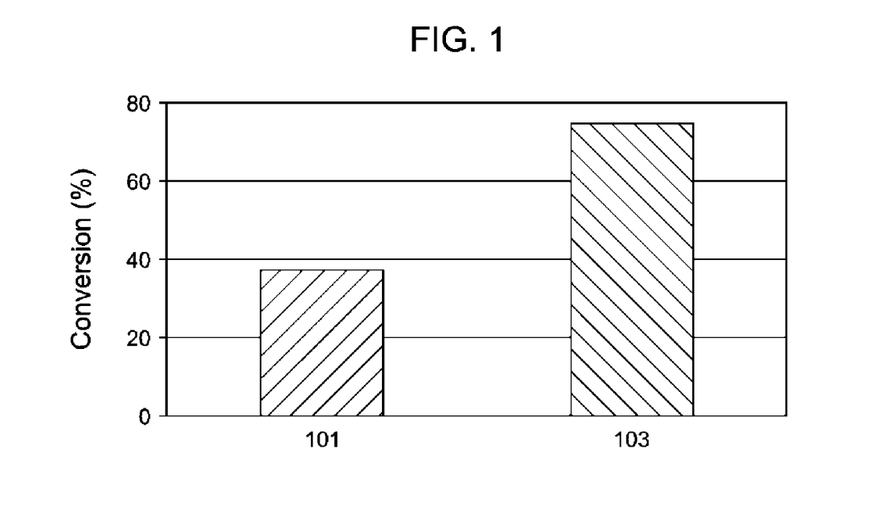
FIGS. 1 and 2 are charts showing conversion and selectivity, respectively, of cyclohexane to benzene using two different catalysts activated by two differing procedures according to the examples in the present disclosure.
Figure 2:
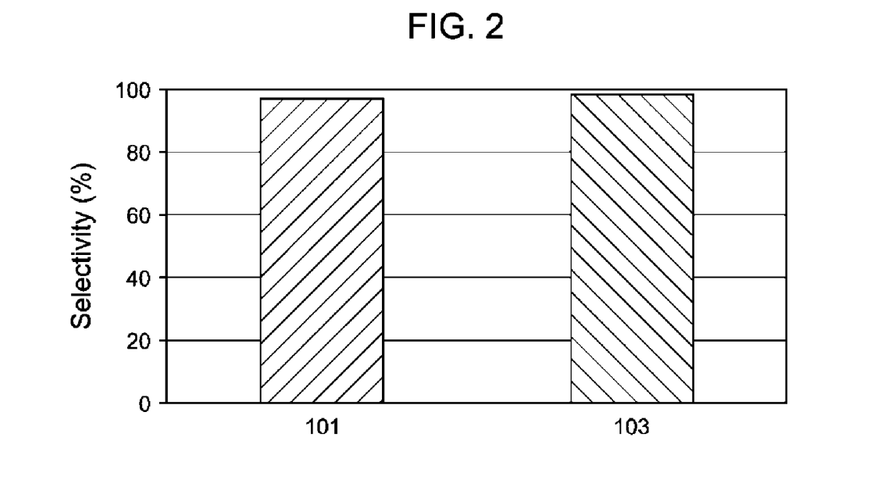

As can be seen from FIG. 1, catalyst activity was nearly doubled when the catalyst was activated using Procedure B as compared as procedure A. As can be seen from FIG. 2, the improved activity was achieved with no loss in selectivity.

Thus, is it clear from these examples that a higher activation temperature higher than 400° C. can be more advantageous than below 400° C.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The contents of all references cited herein are incorporated by reference in their entirety.

Non-limiting embodiments of the processes of the present disclosure include:

E1. A dehydrogenation process, the process comprising:

(1A) providing a catalyst precursor comprising (i) an inorganic support and (ii) 0.05 wt % to 10.0 wt % of a first metal selected from the Groups 6 to 10 metals of the Periodic Table of Elements, the percentages based on the total weight of the catalyst precursor;

(1B) obtaining an activated dehydrogenation catalyst by treating the catalyst precursor at a temperature in a range from 300° C. to 600° C. for a period of at least 15 minutes in a $H_2$-containing atmosphere; and (1C) contacting a first composition with the activated dehydrogenation catalyst in a dehydrogenation reactor under a dehydrogenation condition to convert at least a portion of the cyclohexane to benzene and obtain a dehydrogenation reaction product.

E2. The process of E1, wherein the temperature of step (1B) is in a range from 420° C. to 550° C.

E3. The process of E1 or E2, wherein the first composition in step (1C) is obtained by:

(1Ba) contacting benzene and hydrogen with a hydroalkylation catalyst under a hydroalkylation condition to form a hydroalkylation reaction mixture comprising cyclohexylbenzene, cyclohexane, methylcyclopentane, and benzene; and (1Bb) obtaining from at least a portion of the hydroalkylation reaction mixture (i) a first composition that has a higher concentration of at least one of benzene and cyclohexane than cyclohexylbenzene; and (ii) a second composition that has a higher concentration of cyclohexylbenzene than benzene and cyclohexane.

E4. The process of any of E1 to E3, further comprising:

(1D) recycling at least a portion of the benzene in the dehydrogenation reaction product to step (1Ba).

E5. The process of any of E1 to E4, wherein the inorganic support of the catalyst precursor in step (1A) comprises at least one of: silica; alumina; an aluminosilicate; an oxide of a Group 3-5 metal in the Periodic Table of Elements; carbon; and carbon nanotube.

E6. The process of any of E1 to E5, wherein at least a portion of the first metal in the catalyst precursor in step (1A) is in an oxidation state higher than zero.

E7. The process of any of E1 to E6, wherein the first metal comprises Pt and/or Pd.

E8. The process of any of E1 to E7, wherein the catalyst precursor further comprises at least one of: (iii) from 0.05 wt % to 5.0 wt % of a second metal selected from Group 14 of the Periodic Table of Elements; and (iv) from 0.05 wt % to 10.0 wt % of a third metal selected from the Groups 1 and 2 metals of the Periodic Table of Elements.

E9. The process of E8, wherein the second metal comprises Ge, Sn and/or Pb, and the third metal comprises Na and/or K.

E10. The process of any of E1 to E9, wherein at least 98 wt % of the first metal is the activated catalyst at the completion of step (1B) is in elemental state, the percentage based on the total weight of the first metal.

E11. The process of any of E1 to E10, wherein in step (1B), the $H_2$-containing atmosphere comprises at least 90 wt % of hydrogen.

E12. The process of any of E1 to E11, wherein step (1B) comprises treating the catalyst precursor at a temperature in a range from 300° C. to 600° C. in a flowing stream of $H_2$-containing atmosphere.

E13. The process of any of E1 to E12, wherein the $H_2$-containing atmosphere in step (1B) has a benzene concentration of at most 1 wt %, based on the total weight of the $H_2$-containing atmosphere.

E14. The process of any of E1 to E13, wherein in step (1C), the first composition further comprises hydrogen, and in step (1B), the $H_2$-containing atmosphere is the first composition.

E15. The process of any of E1 to E14, wherein after step (1B) but before (1C), the activated dehydrogenation catalyst is protected by a protective atmosphere free of $O_2$.

E16. The process of E15, wherein the protective atmosphere comprises at least one of $H_2$ and $CH_4$.

E17. The process of any of E1 to E16, wherein step (1B) comprises heating the catalyst precursor at a temperature in a range from 450° C. to 550° C. for at least 15 minutes.

E18. The process of any of E1 to E17, wherein step (1B) comprises heating the catalyst precursor at a first heating rate in a range from 2° C. to 30° C./minute at a temperature below 400° C., and/or a second heating rate in a range from 1° C. to 15° C./minute in a temperature range from 400° C. to 600° C.

E19. The process of any of E1 to E18, wherein step (1A) comprises:

(1A-1) providing the inorganic support;

(1A-2) impregnating the inorganic support with a solution of a salt of the first metal to obtain an impregnated support; and subsequently (1A-3) calcining the impregnated support at a temperature in a range from 500° C. to 1000° C.

E20. The process of any of E1 to E19, wherein steps (1B) and (1C) are both conducted in the dehydrogenation reactor.

E21. The process of any of E1 to E19, wherein in step (1Ba), the first composition further comprises benzene and hydrogen.

E22. The process of any of E1 to E21, wherein in step (1C), the first composition comprises 0.01 wt % to 5.0 wt % methylcyclopentane, the percentages based on the total weight of the first composition, and at least a portion of the methylcyclopentane is converted into a paraffin.

E23. The process of any of E1 to E22, wherein in step (1C), the dehydrogenation condition comprises a temperature in a range from 300° C. to 600° C.

E24. A process for making phenol and/or cyclohexanone, the process comprising:

(2A) producing cyclohexylbenzene according to a process of any of E3 to E23;

(2B) oxidizing at least a portion of the cyclohexylbenene to obtain an oxidation reaction product comprising cyclohexylbenzene hydroperoxide; and (2C) cleaving at least a portion of the cyclohexylbenzene hydroperoxide to produce a cleavage reaction product comprising phenol and cyclohexanone.

E25. A dehydrogenation process comprising:

(3A) providing a catalyst precursor comprising (i) an inorganic support, and (ii) 0.05 wt % to 10.0 wt % of a first metal selected from the Groups 6 to 10 metals of the Periodic Table of Elements, the percentages based on the total weight of the catalyst precursor;

(3B) obtaining an activated catalyst by treating the catalyst precursor at a temperature in a range from 300° C. to 600° C. for a period of at least 15 minutes in a $H_2$-containing atmosphere; and (3C) contacting a first composition comprising at least 0.1 wt % of a saturated cyclic hydrocarbon, the percentage based on the total weight of the composition, with the activated catalyst under a dehydrogenation condition to convert at least a portion of the saturated cyclic hydrocarbon to an unsaturated cyclic hydrocarbon.

E26. The process of E25, wherein the inorganic support of the catalyst precursor comprises at least one of: silica; alumina; an aluminosilicate; and an oxide of a Group 3-5 metal in the Periodic Table of Elements.

E27. The process of E25 or E26, wherein at least a portion of the first metal in the catalyst precursor is in an oxidation state higher than zero.

E28. The process of any of E25 to E27, wherein the first metal comprises Pt and/or Pd.

E29. The process of any of E25 to E28, wherein the catalyst precursor further comprises at least one of: (iii) from 0.05 wt % to 5.0 wt % of a second metal selected from Group 14 of the Periodic Table of Elements; and (iv) from 0.05 wt % to 10.0 wt % of a third metal selected from the Groups 1 and 2 metals of the Periodic Table of Elements.

E30. The process of E29, wherein the second metal comprises Ge, Sn and/or Pb, and the third metal comprises Na and/or K.

E31. The process of any of E25 to E30, wherein at least 98 wt % of the first metal is the activated catalyst at the completion of step (3B) is in elemental state, the percentage based on the total weight of the first metal.

E32. The process of any of E25 to E31, wherein the $H_2$-containing atmosphere has a benzene concentration of at most 1 wt %, based on the total weight of the $H_2$-containing atmosphere.

E33. The process of any of E25 to E32, wherein in step (1Bb), the first composition further comprises hydrogen, and in step (1B), the $H_2$-containing atmosphere is the first composition.

E34. The process of any of E25 to E33, wherein after step (1B) but before (1C), the activated dehydrogenation catalyst is protected by a protective atmosphere free of $O_2$.

E35. The process of E34, wherein the protective atmosphere comprises at least one of $H_2$ and $CH_4$.

E36. The process of any of E25 to E35, wherein step (3B) comprises treating the catalyst precursor at a temperature in a range from 300° C. to 600° C. in a flowing stream of $H_2$-containing atmosphere.

E37. The process of any of E25 to E37, wherein step (3B) comprises heating the catalyst precursor at a temperature in a range from 450° C. to 550° C. for at least 15 minutes.

E38. The process of any of E254 to E37, wherein step (3B) comprises heating the catalyst precursor at a first heating rate in a range from 2° C. to 30° C./minute at a temperature below 400° C., and/or a second heating rate in a range from 1° C. to 15° C./minute in a temperature range from 400° C. to 600° C.

E39. The process of any of E25 to E38, wherein step (3A) comprises:

(3A-1) providing the inorganic support;

(3A-2) impregnating the inorganic support with a solution of a salt of the first metal to obtain an impregnated support; and subsequently (3A-3) calcining the impregnated support at a temperature in a range from 500° C. to 1000° C.

E40. The process of any of E25 to E39, wherein steps (3B) and (3C) are conducted in the same vessel.

E41. The process of E40, wherein between steps (3B) and (3C), the activated catalyst is protected from exposure to oxygen.

E42. The process of any of E25 to E41, wherein in step (3C), the composition comprises cyclohexane, benzene and hydrogen, and at least a portion of the cyclohexane is converted to benzene.

E43. The process of any of E25 to E42, wherein in step (3C), the composition comprises methylcyclopentane, and at least a portion of the methylcyclopentane is converted into a paraffin.

E44. The process of any of E25 to E43, wherein in step (3C), the dehydrogenation condition comprises a temperature in a range from 300° C. to 600° C.

E45. The process of any of E25 to E44, wherein the first metal is Pt and/or Pd.

The invention claimed is:

1. A dehydrogenation process, the process comprising:
   (1A) providing a catalyst precursor comprising (i) an inorganic support, and (ii) 0.01 wt % to 10.0 wt % of a first metal selected from the Groups 6 to 10 metals of the Periodic Table of Elements based on the total weight of the catalyst precursor;
   (1B) obtaining an activated dehydrogenation catalyst by treating the catalyst precursor at a temperature in a range from 450° C. to 600° C. for a period of at least 15 minutes in a $H_2$-containing atmosphere; and
   (1C) contacting a first composition comprising cyclohexane with the activated dehydrogenation catalyst in a dehydrogenation reactor under a dehydrogenation condition to convert at least a portion of the cyclohexane to benzene and obtain a dehydrogenation reaction product.

2. The process of claim 1, wherein the temperature of step (1B) is in a range from 450° C. to 550° C.

3. The process of claim 1, wherein the first composition in step (1C) is obtained by:
   (1Ba) contacting benzene and hydrogen with a hydroalkylation catalyst under a hydroalkylation condition to form a hydroalkylation reaction mixture comprising cyclohexylbenzene, cyclohexane, methylcyclopentane, and benzene; and
   (1Bb) obtaining from at least a portion of the hydroalkylation reaction mixture (i) a first composition that has a higher concentration of at least one of benzene and cyclohexane than cyclohexylbenzene; and (ii) a second composition that has a higher concentration of cyclohexylbenzene than benzene and cyclohexane.

4. The process of claim 3, further comprising:
   (1D) recycling at least a portion of the benzene in the dehydrogenation reaction product to step (1Ba).

5. The process of claim 1, wherein the first metal comprises Pt and/or Pd.

6. The process of claim 1, wherein at least a portion of the first metal in the catalyst precursor in step (1A) is in an oxidation state higher than zero.

7. The process of claim 1, wherein the catalyst precursor further comprises at least one of: (iii) from 0.01 wt % to 5.0 wt % of a second metal selected from Group 14 of the Periodic Table of Elements; and (iv) from 0.01 wt % to 10.0 wt % of a third metal selected from the Groups 1 and 2 metals of the Periodic Table of Elements.

8. The process of claim 7, wherein the second metal comprises Sn and the third metal comprises K.

9. The process of claim 1, wherein in step (1B), the $H_2$-containing atmosphere comprises at least 90 wt % of hydrogen.

10. The process of claim 1, wherein step (1B) comprises treating the catalyst precursor in a flowing stream of $H_2$-containing atmosphere.

11. The process of claim 1, wherein the $H_2$-containing atmosphere in step (1B) has a benzene concentration of at most 1 wt %, based on the total weight of the $H_2$-containing atmosphere.

12. The process of claim 3, wherein in step (1Bb) the first composition further comprises hydrogen, and in step (1B) the $H_2$-containing atmosphere is the first composition.

13. The process of claim 1, wherein after step (1B) but before step (1C), the activated dehydrogenation catalyst is protected by a protective atmosphere free of $O_2$.

14. The process of claim 13, wherein the protective atmosphere comprises at least one of $H_2$ and $CH_4$.

15. The process of claim 1, wherein step (1A) comprises:
(1A-1) providing the inorganic support;
(1A-2) impregnating the inorganic support with a solution of a salt of the first metal to obtain an impregnated support; and
(1A-3) calcining the impregnated support at a temperature in a range from 300° C. to 1000° C.

16. The process of claim 1, wherein steps (1B) and (1C) are both conducted in the dehydrogenation reactor.

17. The process of claim 1, wherein in step (1Ba) the first composition comprises benzene and hydrogen.

18. The process of claim 1, wherein in step (1C), the first composition comprises 0.01 wt % to 5.0 wt % methylcyclopentane based on the total weight of the first composition, and at least a portion of the methylcyclopentane is converted into a paraffin.

19. The process of claim 1, wherein in step (1C), the dehydrogenation condition comprises a temperature in a range from 300° C. to 600° C.

20. A process for making phenol and/or cyclohexanone, the process comprising:
(2A) producing cyclohexylbenzene from the second composition obtained in step (1Bb) according to the process of claim 3;
(2B) oxidizing at least a portion of the cyclohexylbenene to obtain an oxidation reaction product comprising cyclohexylbenzene hydroperoxide; and
(2C) cleaving at least a portion of the cyclohexylbenzene hydroperoxide to produce a cleavage reaction product comprising phenol and cyclohexanone.

* * * * *